United States Patent [19]
Fang et al.

[11] Patent Number: 5,981,280
[45] Date of Patent: Nov. 9, 1999

[54] METHOD AND CONSTRUCTS FOR INHIBITING PROTEIN EXPRESSION IN BACTERIA

[75] Inventors: Li Fang, Allentown, Pa.; Weining Jiang, New York, N.Y.; Masanori Mitta, Kyoto, Japan; Masayori Inouye, Bridgewater, N.J.

[73] Assignee: The University of Medicine and Denistry of New Jersey, Piscataway, N.J.

[21] Appl. No.: 08/769,945

[22] Filed: Dec. 19, 1996

Related U.S. Application Data

[60] Provisional application No. 60/013,922, Mar. 22, 1996.
[51] Int. Cl.[6] .............................. C12N 15/09; C12N 1/21; C07H 21/02; C07H 21/04
[52] U.S. Cl. .................. 435/471; 435/252.3; 435/320.1; 536/23.1; 536/24.1; 536/24.5; 536/25.1
[58] Field of Search .............................. 435/6, 29, 172.3, 435/252.3, 252.33, 320.1, 471, 476; 536/23.1, 23.7, 24.1, 24.5, 25.1; 935/38, 44

[56] References Cited

U.S. PATENT DOCUMENTS 5,714,575  2/1998  Inouye et al. ........................... 530/300

OTHER PUBLICATIONS

Schroeder et al. (1993) Gene, 136: 277–280.
Willimsky et al. (1992) J. Bacteriol. 174: 6326–6335.
Sakura et al. (1988) Gene, 73: 499–507.
Tafuri et al. (1990), PNAS, 87: 9028–9032.
Av–Gay et al. (1992), Nucleic Acid Res., 20: 5478.
Murray et al. (1992) PNAS, 89: 11–15.
Didier et al. (1988) PNAS, 85:7322–7326.
Wistow et al. (1990) Nature, 344: 823–824.
Schuchel et al. (1993) Nature, 364: 169–171.
Goldstein et al. (1990), PNAS, 87: 283.
Lane, et al., (1985) "Rapid Determination of 165 Ribosomal RNA Sequences for Phylogenetic Analyses", PNAS, 82:6955–6959.
Spregart, et al., (1996) "The Downstream Box: an Efficient and Independent Translation Initiation Signal in *Escherichia coli*", The EMBO Journal, 15(3):665–674.
Olsen, et al., (1993) "Ribosomal RNA: a Key to Phylogeny", The FASEP Journal, 7:113–123.
Durand, et al., (1996) "Bacterial host specificity of Lucinacea Endosymbionts: Interspecific variation in 165 rRNA Sequences", FEMS Microbiology Letters, 140:193–198.
Bottger, Erik C. (1989) "Rapid Determination of Bacterial Ribosomal RNA Sequences by Direct Sequencing of Enxymatically Aplified DNA", FEMS Microbiology Letters, 65:171–176.
Stackebrandt, et al. (1994) "Taxomic Note: A sequence Analysis in the Present Specied Sefinition in Bacteriology", International Journal of Systematic Bacteriology, 44(4):846–849.
Jiang, et al., (1996) "The Role of the 5'–End Untranslated Region of the mRNA for CspA, the Major Cold–Shock Protein of *Escherichia coli*, in Cold–Shock Adaptation", Journal of Bacteriology, 176(16):4919–4925.
Jones, et al., (1996) "RbfA, a 30S Ribosomal Binding Factor, is a Cold–Shock Protein Whose Absence Triggers the Cold–Shock Response", Molecular Microbiology, 21(6):1207–1218.

*Primary Examiner*—Nancy Degen
*Assistant Examiner*—Thomas G. Larson
*Attorney, Agent, or Firm*—Weiser and Associates, P.C.

[57] ABSTRACT

A method of inhibiting the translation of bacterial mRNA is disclosed, which method comprises overexpressing in a bacterium an mRNA which contains a sequence which is complementary to the anti-downstream box region of the 16S rRNA. RNA and DNA constructs for the overexpression of the mRNA of the invention are disclosed.

41 Claims, 6 Drawing Sheets

5,981,280

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:1:

ACUUUGUGAU UCAU                     14

(2) INFORMATION FOR SEQ ID NO:2:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:2:

AUGACUGGUA UUGU                     14

(2) INFORMATION FOR SEQ ID NO:3:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:3:

AUGACUGGUU UCGU                     14

(2) INFORMATION FOR SEQ ID NO:4:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:4:

AUGACUGGUU UAGU                     14

(2) INFORMATION FOR SEQ ID NO:5:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:5:

AUGAGUUAUG UAGA                     14

(2) INFORMATION FOR SEQ ID NO:6:

(i) SEQUENCE CHARACTERISTICS:

(A) LENGTH: 14 base pairs
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO:6:

AUGGCGAAAA GAAU                                                              14

(2) INFORMATION FOR SEQ ID NO:7:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: mRNA (ix) FEATURE:
            (A) NAME/KEY: misc_difference
            (B) LOCATION: 4 to 33
            (D) OTHER INFORMATION: /note= "N = G,C,U or A;
                  any number or all N in positions 4 to 33 inclusive
                  may be absent, each occurrence of N may be same or
                  different from any other occurrence"

(xi) SEQUENCE DESCRIPTION: SEQ ID NO:7:

AUGNNNNNNN NNNNNNNNNN NNNNNNNNNN NNNAUGACUG GUAUCGU                          47

(2) INFORMATION FOR SEQ ID NO:8:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_difference
            (B) LOCATION: 4 to 33
            (D) OTHER INFORMATION: /note= "N = G,C,T or A;
                  any number or all N in positions 4 to 33 inclusive
                  may be absent, each occurrence of N may be same or
                  different from any other occurrence"

(xi) SEQUENCE DESCRIPTION: SEQ ID NO:8:

ATGNNNNNNN NNNNNNNNNN NNNNNNNNNN NNNATGACTG GTATCGT                          47

(2) INFORMATION FOR SEQ ID NO:9:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

AATTATTAAA GGTAA                                                             15

(2) INFORMATION FOR SEQ ID NO:10:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:10:

AATTTCTAGA GGTAA                                                          15

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GACAGGATTA AAAATCGATG                                                     20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

TTTAGAGCCA TCGTCAGGAG                                                     20

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

ACGATACCAG TCGATTTTAC CGGAC                                               25

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

CTGTCGACTT ACTTACGGCG TTGC                                                24

(2) INFORMATION FOR SEQ ID NO:15:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:15:

AUGACUGGUA UCGU                                          14

(2) INFORMATION FOR SEQ ID NO:16:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:16:

UACUUAGUGU UUCA                                          14

(2) INFORMATION FOR SEQ ID NO:17:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

ATGACTGGTA TCGT                                          14

(2) INFORMATION FOR SEQ ID NO:18:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

ATGACTGGTT TCGT                                          14

(2) INFORMATION FOR SEQ ID NO:19:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

ATGACTGGTT TAGT                                          14

(2) INFORMATION FOR SEQ ID NO:20:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

ATGAGTTATG TAGA                                          14

(2) INFORMATION FOR SEQ ID NO:21:

```
    (i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

ATGGCGAAAA GAAT                                                              14
```

METHOD AND CONSTRUCTS FOR INHIBITING PROTEIN EXPRESSION IN BACTERIA

This application is a continuation in part application of and claims the priority date of pending provisional application Ser. No. 60/013,922, filed Mar. 22, 1996, which application is incorporated herein by reference.

FIELD OF THE INVENTION

The present invention relates to the field of biotechnology, and more particularly to the field of regulating the translation of mRNA and the production of proteins.

BACKGROUND OF THE INVENTION

Bacteria are the causative agents for a great many diseases in plants and animals, including humans. Before the advent of antibiotics, such as penicillin, bacterial infections were considered to be non-treatable. Since that time, additional antibiotics have been developed to control and kill bacteria and treat bacterial infections.

Unfortunately, however, many antibiotics have proven over time to be less and less effective at controlling bacterial populations due to the development of resistance of the bacteria to the antibiotics. Bacterial resistance occurs because antibiotic therapy naturally kills most easily and swiftly the bacteria which are most sensitive to the antibiotic, leaving behind the bacteria which are less affected by the antibiotic therapy. Additionally, certain bacteria can pass antibiotic resistance genes to other otherwise sensitive bacteria. Over time, the populations of antibiotic sensitive bacteria tend to disappear, leaving only resistant populations.

Science has responded by discovering newer and better antibiotics with which to treat resistant bacteria. However, it appears that, as fast as new antibiotics can be produced, resistant strains of bacteria develop. Therefore, there is a clear and pressing need for new means of killing harmful bacteria.

The present invention provides a novel mechanism for killing bacteria by disrupting bacterial protein production. The risk of development of bacterial resistance to the compounds and method of the invention is minimized, as compared to that encountered with traditional antibiotics, because the invention takes advantage of natural processes of the bacteria.

SUMMARY OF THE INVENTION

It has been unexpectedly discovered that protein synthesis in bacteria can be inhibited or even completely stopped by overexpressing in the bacteria an RNA comprising a sequence which is substantially complementary to a portion of the bacterial 16S rRNA adjacent to the decoding region, which portion is known as the anti-downstream box (ADB). The RNA sequence which is substantially complementary to the ADB is referred as a downstream box (DB) because, in a naturally occurring bacterial mRNA, the DB is positioned downstream from the initiation codon of the mRNA. The structure of the 3' region of 16S rRNA and the function of the DB box as a translation initiation signal in bacteria is described in Sprengart, et al., EMBO Journal, 15(3) :665–674 (1996), which is incorporated herein by reference.

The present invention comprises several embodiments. In one embodiment, the invention is a method for arresting or inhibiting the production of bacterial proteins. The method of the invention comprises overexpressing in a bacterial cell an mRNA which comprises an initiation codon and a downstream box. The downstream box is preferably 3' to the initiation codon, with an intervening nucleotide sequence of 0 to 30 nucleotides. Alternatively, the downstream box may overlap the initiation codon. In this latter situation, any or all of the three nucleotides of the initiation codon may constitute the 5' end of the downstream box. The DB of the overexpressed mRNA is allowed to anneal to the ADB, thereby effectively binding the 16S rRNA and preventing translation of other mRNAs, ultimately preventing production of bacterial proteins.

In another embodiment, the invention is an oligonucleotide mRNA construct for the inhibition of protein synthesis in bacteria. The RNA construct has a nucleotide sequence which comprises an initiation codon and a DB sequence 3' to, or overlapping, the initiation codon. Preferably, the RNA construct is free of a site for RNA endonucleases.

In another embodiment, the invention is an oligonucleotide DNA construct, which DNA construct codes for an mRNA which comprises an initiation codon and a DB sequence 3' to, or overlapping, the initiation codon.

In a further embodiment, the invention is a vehicle for transforming a bacterial cell, which vehicle contains a DNA promoter sequence which is operably linked to a DNA sequence which codes for an mRNA which comprises an initiation codon and a DB sequence 3' to, or overlapping, the initiation codon.

A further embodiment is a bacterial cell which has been transformed with a vehicle containing a DNA promoter sequence which is operably linked to a DNA sequence which codes for an mRNA which comprises an initiation codon and a DB sequence 3' to or overlapping the initiation codon.

The invention is applicable to, and can be practiced in, all bacteria because of the existence of the 16S rRNA, which is a well conserved sequence. Thus, the practice of the invention is not dependent on the bacteria species used, such as *E. coli*, which is used herein to illustrate the invention. See, Goodfellow and O'Donnell, Handbook of New Bacterial Systematics, Academic Press (1993); Stackebrandt and Goebel, International Journal of Systematic Bacteriology, 44 (4): 846–849 Duran and gros, FEMS Microbiology Letters, 140:193–198 (1996); and Olsen and Woese, FASEB Journal, 7:113–123 (1993), each of which is incorporated herein by reference. The fact that bacteria in which the 16S rRNA is highly homologous with respect to that of *E. coli* includes mammalian pathogens such as Mycobacterium spi. and *Legionella pneumophila*, and even non-pathogen symbionts of marine animals, such as *Linga pensylvanica* and *Bathymodiolus thermophilus*, is indicative of the highly conserved nature of the 16S rRNA and the general applicability of the present invention. The conserved nature of the 16S rRNA permits identification of the ADB in a given bacteria from the nucleotide sequence of the 16S rRNA which can be found for bacteria in the GenBank database. Means of determining the nucleotide sequence of the 16S rRNA are known. See, for example, Lane et al., Proc. Natl. Acad. Sci., 82:6955–6959 (1985), and Bottger, FEMS Microbiology Letters, 65:171–176 (1989), each of which is incorporated herein by reference. The bacterial 16S rRNA contains, at its 3' end, an anti-Shine-Dalgarno region (SD) and a decoding region. The ADB is a 12 to 14 nucleotide long region close to the decoding region of 16S rRNA. Once the ADB is identified and its sequence ascertained, the constructs of the invention may be readily constructed for any particular bacteria, as may the vehicle of the invention, and the method of the invention may likewise be practiced in any bacteria.

Moreover, because of the highly conserved nature of the sequence of the 3' end region of the 16S rRNA, it is conceived that a DB which is substantially complementary to the ADB of the 16S rRNA of any one particular bacterial species will be sufficiently complementary to the ADB of the 16S rRNA of a second bacterial species to enable the method of the invention to be practiced in different species of bacteria using a DB of the same or similar sequence.

DETAILED DESCRIPTION OF THE INVENTION

Figure 1:
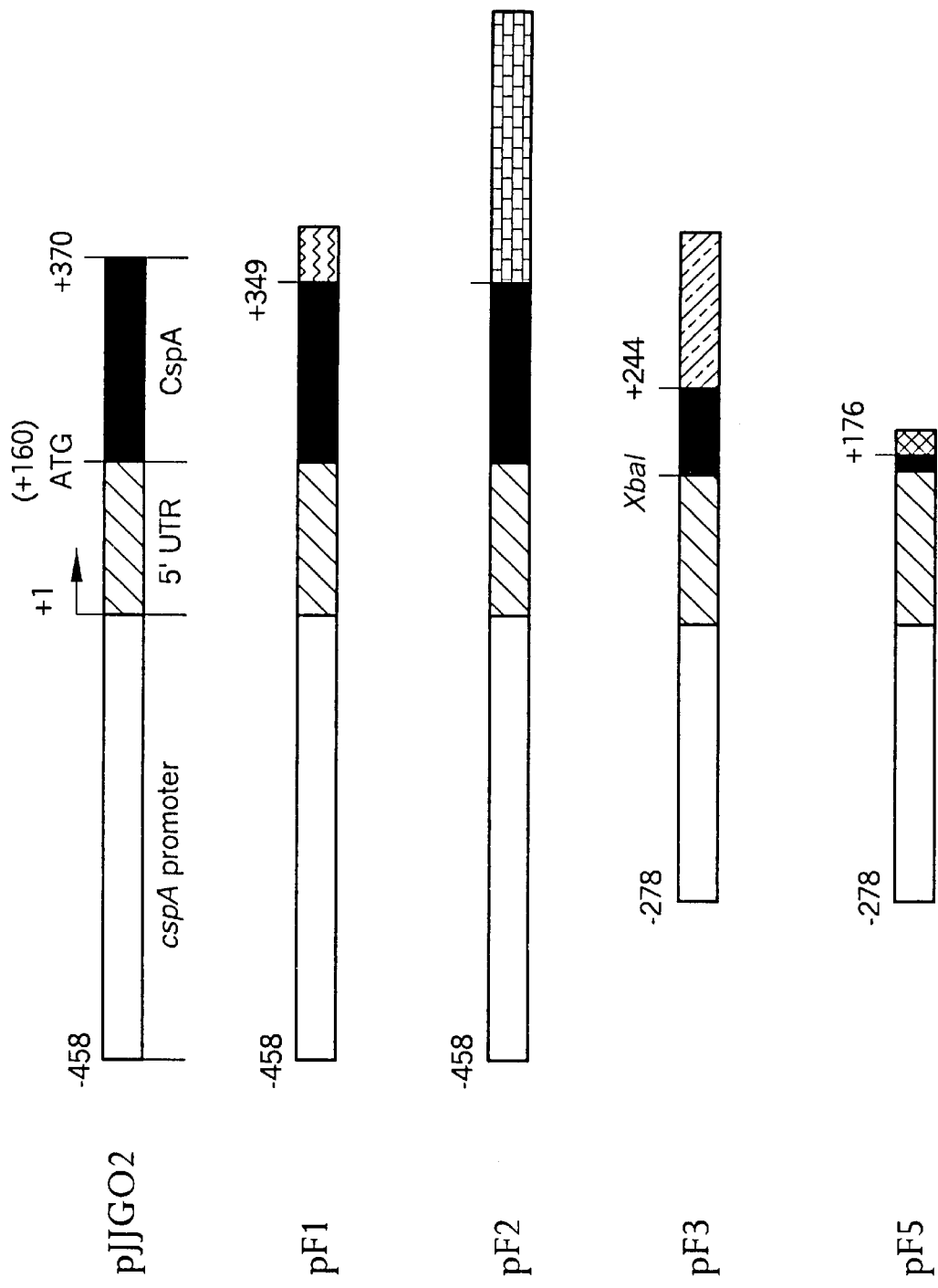
FIG. 1 shows diagrammatically the construction of DNA sequences overexpressing mRNAs of the invention.

As previously reported by Sprengart et al., the downstream box (DB) of bacteria plays an important role in the translation of mRNA to produce proteins. The DB binds to a portion of the bacterial 16S rRNA near the 3' end and is thought to help position the mRNA and rRNA in proper relative position for translation to occur.

In accordance with the present invention, it has been discovered that during the time when the ADB is annealed to the DB of an overexpressed mRNA, the 16S rRNA is not capable of participation in the translation of cellular mRNAs other than the annealed overexpressed mRNA. It has been further discovered that the entire protein-making machinery of a bacterium may be shut down by providing to the bacterium an mRNA, which encodes a DB which is substantially complementary to the ADB of the 16S rRNA, which anneals to all or substantially all of the bacterial 16S rRNA.

Whenever the term "complementary" is used herein, it is intended to include "substantially complementary". Thus, the term "complementarity" does not require perfect complementarity. It is sufficient that the two sequences be "complementary" as defined in Kahl, Dictionary of Gene Technology, VCH Publishers, Inc. (1995), which is incorporated herein by reference. That is, two nucleotide sequences are complementary if they are capable of forming a hydrogen-bonded duplex with each other according to Watson-Crick base-pairing rules. Two complementary RNA sequences, or an RNA and a DNA sequence, will form pairings of A-U, G-C, or G-U. "Complete complementarity" is not required.

As is known, the ADB is a nucleotide sequence of about 14 bases which is positioned in the 3' end of the 16S rRNA, in close proximity to the decoding region of 16S rRNA. The 16S rRNA nucleotide sequence of known bacteria is known and can be found in the GenBank database. Thus, for a selected bacterium, the ADB can be readily identified by comparison to the sequence of the ADB in a bacterium in which the sequence is known, for example E. coli. Once the ADB is identified, a DB complementary to the ADB can be constructed, and incorporated into an appropriate mRNA, as described below.

The mRNA of the invention is an isolated mRNA or an mRNA which has been transcribed from an isolated DNA. The mRNA comprises an initiation codon, which codon is preferably AUG. Other suitable initiation codons for the mRNA include GUG and UUG.

The mRNA of the invention further comprises a downstream box sequence, which is typically 3' to the initiation codon. The codons of the DB may or may not be in phase with the initiation codon. The DB sequence may be immediately adjacent to the initiation codon so that there are no intervening nucleotides. Generally, the DB is separated from the initiation codon by an intervening nucleotide sequence between 1 and 30 nucleotides long. The base sequence of the intervening sequence is immaterial and may be constituted of any sequence of nucleotides. Preferably, the intervening nucleotide sequence is 9 to 15 nucleotides in length, with a most preferred length of 12 nucleotides. Alternatively, the DB may overlap the initiation codon. That is, any one of the three nucleotides of the initiation codon of the mRNA of the invention may form the 5' end of the DB.

The DB sequence of the mRNA of the invention is a nucleotide sequence which is complementary to the ADB of the 16S rRNA of a bacterium. Generally, the DB is between 6 and 20 bases long, preferably between 8 and 14 bases long, although the DB may be longer than 20 bases. For example, the DB may comprise nucleotides which are complementary to nucleotides 3' or 5', or both, to the ADB. Regardless of length of the DB, a higher degree of complementarity between the DB and the ADB is associated with more effective annealing, resulting in more efficient inhibition of bacterial protein synthesis, in accordance with the method of the invention.

In addition to the initiation codon, the DB, and any intervening sequence, the mRNA construct of the invention may comprise a nucleotide sequence 5' to the initiation codon or 3' to the DB. For example, the mRNA construct may comprise a sequence 3' to the DB which encodes a polypeptide or may comprise a termination codon. Likewise, the mRNA construct may comprise an untranslated sequence and/or a Shine-Dalgarno sequence 5' to the initiation codon.

The length of the mRNA construct, including the initiation codon, any intervening sequence, and DB, and exclusive of any additional nucleotides at the 5' or 3' end, may be any length between 8 nucleotides to about 45 nucleotides. Of course, if the mRNA comprises a 5' or 3' sequence in addition to the above essential components, such as a Shine-Dalgarno sequence, the mRNA may be much longer, up to several hundreds of nucleotides in length.

Preferably, although not necessarily, the mRNA construct is free of sites for RNA endonucleases. It is especially preferred that the portion of the mRNA construct comprising the essential portions of the construct, that is the initiation codon and the DB, be free of sites for RNA endonucleases, which might otherwise degrade the mRNA construct and free the bacterial 16S rRNA to bind to bacterial mRNAs.

The mRNA construct of the invention may have a sequence which is similar or identical to an mRNA sequence found naturally in a bacterium. For example, the mRNAs for several cold-shock proteins, such as the mRNAs for E. coli proteins CspA, CspB, CspG, CsdA, and RbfA, comprise a Shine-Dalgarno sequence, an initiation codon, and a downstream box substantially complementary to the antidownstream box of the *E. coli* 16S rRNA. Other *E. coli* mRNAs which contain a Shine-Dalgarno sequence, an initiation codon, and a downstream box complementary to the *E. coli* ADB include RecA, Hns, NusA, InfB, and CspD.

Below are several non-limiting examples of suitable DBs for the mRNA construct. Each of the following DB is substantially complementary to the ADB of the *E. coli* 16S rRNA which ADB has the sequence:

ADB 3' (−1481) UACUUAGUGUUUCA (−1469) 5' (SEQ ID NO: 16).

DB #1: 5' AUGACUGGUAUCGU 3' (SEQ ID NO: 15)

DB #2: 5' AUGACUGGUUUCGU 3' (SEQ ID NO: 3)

DB #3: 5' AUGACUGGUUUAGU 3' (SEQ ID NO: 4)

DB #4: 5' AUGAGUUAUGUAGA 3' (SEQ ID NO: 5)

DB #5: 5' AUGGCGAAAAGAAU 3' (SEQ ID NO: 6)

A suitable mRNA construct according to the invention can be constructed using any one of the above DBs, or other suitable DB, for example:

5' AUGXXXXXXXXXXXXXXXXXXXXXX-XXXXXXXXAUGACUGGUAUCGU 3' (SEQ ID NO: 7)

where X is G, C, U, or A, wherein each occurrence of X may be the same as or different from any other occurrence of X. Alternatively, the 5' end of the DB overlaps the initiation, codon.

The DNA of the invention is any isolated DNA which encodes for an mRNA which is suitable for the mRNA construct of the invention, as described above. The DNA may further comprise an additional nucleotide sequence 5' to the initiation codon, which sequence may include a promoter sequence. Such promoter sequences may be used to control transcription of the mRNA construct. The DNA may comprise a sequence 5' to the initiation codon which sequence has a function other than as a promoter, such as a Shine-Dalgarno sequence, and/or a sequence which has no known function. The DNA may comprise a sequence 3' to the portion encoding the DB of the mRNA construct, which sequence may include, for example, a termination codon, or may encode a polypeptide, and a sequence required for transcription termination.

An example of a suitable DNA which encodes for the mRNA construct of the invention is:

5' ATGYYYYYYYYYYYYYYYYYYYYYYY-YYYYYYYATGACTG GTATCGT 3' (SEQ ID NO: 8)

where Y is G, C, T, or A, wherein each occurrence of Y may be the same as or different from any other occurrence of Y. Alternatively, the 5' end of the DB overlaps the initiation codon, ATG. The DNA may contain additional sequences, as stated above, at the 5' and/or 3' end of the DNA.

The DNA sequence of the invention may be contained within a vehicle or cloning vector, such as in a plasmid or phage vector.

The DNA sequence in the vector may be under the control of a promoter sequence located 5' to the initiation codon. These vectors containing the DNA of the invention may be used to transform a host bacterium which may be used to overexpress the mRNA of the invention, that is to produce the mRNA in the bacterium at levels higher than produced in similar non-transformed bacteria. Any bacterium which may be transformed by means of a cloning vector is a suitable host for the DNA sequence of the invention. Methods of producing cloning vectors and transforming bacteria are known in the art and are taught, for example, in Ausubel et al., Current Protocols in Molecular Biology, J. Wiley & Sons, Inc. (1995), which is incorporated herein by reference.

Overexpression of the mRNA sequence of the invention results in the production of the mRNA in an amount which is higher than that found normally in the bacteria. To whatever extent the mRNA is overexpressed, the production of bacterial proteins is inhibited. If the mRNA is expressed at a high enough level, production of bacterial proteins will be completely stopped, which may lead ultimately to death of the bacterium.

Therefore, the construct producing the mRNA is useful as an antibiotic to kill or to stop the growth of bacteria. The construct producing the mRNA may be packaged in a bacteriophage which would permit the mRNA to be used as a disinfectant or as a topical antibiotic preparation. It is conceivable that strategies for delivery will be devised to permit transformation of bacteria which are causing infection of a plant or animal, such as a mammal like humans, dogs, cats, cattle, horses, and livestock. Such antibiotics are safe for use in eukaryotes, as eukaryotes lack the 16S rRNA that is present in bacteria.

According to the method of the invention, an mRNA comprising an initiation codon and a DB which is complementary to the ADB of the 16S rRNA of a bacterium, is caused to be overexpressed in a bacterium, and is then allowed to anneal to the ADB of the 16S rRNA of the bacterium, thereby inhibiting production of proteins encoded by other mRNAs in the bacterium.

Any means of delivery which results in overexpression of the mRNA of the invention is suitable for the method of the invention. For example, the bacterium may be transformed by means of a vehicle harboring a DNA sequence which codes for the mRNA of the invention.

If desired, expression of the mRNA sequence of the invention is controlled by placing the DNA sequence under the control of an inducible promoter. For example, if it is desired to kill a harmful bacterium or block its growth while sparing a beneficial bacterium, the DNA sequence may be placed under the control of a promoter which is responsive to a product which is present only in the first bacterium. In this way, the lethal antibiotic effect of the mRNA of the invention will affect only the undesirable, harmful bacterium.

Another means of controlling the expression of the protein production-inhibiting mRNA sequence is to employ a DNA sequence which codes for an mRNA which is unstable under certain conditions.

For example, the 5' untranslated region (5' UTR) of the mRNA of the *E. coli* cold-shock protein, CspA, contains a region immediately 5' to the Shine-Dalgarno region which is susceptible to degradation, presumably by RNAase E, at physiologic growth temperatures of about 37° C. Therefore, the cspA mRNA containing the 5' UTR is unstable under normal growth conditions, having a half life estimated to be approximately 12 seconds. Other cold-shock proteins, such as *E. coli* CspB and CsdA, are similarly unstable at physiologic growth temperatures due to instability of their mRNA. Upon cold shock, such as when the temperature is reduced to 15° C., the half life of the cspA mRNA increases dramatically, to about 15 minutes, an increase in stability of about 75 times over the mRNA at normal physiologic growth temperatures.

Because of the instability at 37° C. of an mRNA containing the 5' UTR of cspA mRNA, this region, or the 5' UTR of the cspB or csda mRNA, can be used to control the expression of the mRNA sequence of the invention, so that its antibiotic effect occurs only below physiologic growth temperatures, such as under cold-shock conditions. The antibiotic effect of the method of the invention is augmented at cold-shock conditions because a cold-shocked bacterium requires new ribosomal factors, whose synthesis is blocked by overproduction of an mRNA containing the DB sequence.

The antibiotic effect of the method of the invention in which the mRNA of the invention is caused to be overexpressed within a bacterium is increased concomitantly with an increase in copy number of the mRNA which is to be expressed. That is, whereas a minimal overexpression of the mRNA of the invention will inhibit the production of proteins by the bacterium, such an inhibition may not be sufficient to prevent further growth of the bacterium or to kill the bacterium. Higher levels of expression of the mRNA result are positively correlated with increased inhibition of protein production. When the copy number is sufficiently high in the bacterium, protein production will be completely blocked.

A similar effect is noted with respect to complementarity of the DB of the overexpressed mRNA and the ADB of the bacterial 16S rRNA. Overexpression of an mRNA comprising a DB with 100% complementarity will be more efficient in binding to the ADB than will be an mRNA comprising a DB with lesser, say 75% complementarity. Thus, the protein blocking effect of an mRNA having a more highly complementary DB will be more pronounced compared to that of an mRNA having a less complementary DB. Therefore, when using an mRNA having a less complementary DB, it may be necessary to express the mRNA in a higher copy number to achieve the same or similar antibiotic results as with an mRNA having a more complementary DB.

The invention is illustrated by the following non-limiting examples.

EXAMPLE 1
E. coli Strain and Culture Media

E. coli CL83 [recA ara (lac-proAB) rpsL(=strA) (φ80 lacZ M15] (Lerner and Inouye, Nuc. Acids Res., 18:4631 (1990)) was used for all experiments and was grown in M9-Casamino acids medium (Miller, J H, Experiments in Molecular Genetics, Cold Spring Harbor Laboratory, Cold Spring Harbor, N.Y. (1972)). For pulse-labeling experiments, a complete amino acid mixture except for methionine was used. The final concentration of each amino acid was 50 mg/ml. Pulse-labeling experiments and SDS-polyacrylamide gel electrophoresis (SDS-PAGE) were carried out as described in Jiang et al., J. Bacteriol., 175:5824–5828 (1993), incorporated herein by reference.

EXAMPLE 2
Plasmid Constructions

The following plasmid constructions are shown diagrammatically in FIG. 1.

Plasmid pF1 was constructed as follows: pJJG02 (Goldstein et al., P.N.A.S., 87:283–287 (1990)) which contains the wild type cspA was digested by PvuII. The released 898-bp fragment contains the cspA gene from −458 to +348 bp (as the transcription initiation site is defined +1) which includes the entire cspA promoter, the 5' untranslated region including the Shine-Dalgarno region, and the CspA sequence for N-terminal 63 amino acid residues. Subsequently, this fragment was recloned into pUC19 digested with PvuII. As a result, the CspA N-terminal 63-residue sequence was fused with a 19-residue sequence from lacZ sequence which was resulted from +1 frame shift on lacZ at base 308 pUC19 sequence (Yanisch-Perron et al., Gene, 33:103 (1985)).

pF2 was constructed in a similar way as that of pF1, except that the 898-bp fragment was recloned into the SmaI site of pUC19 instead of PvuII. As a result, the CspA N-terminal 63-residue sequence was fused with an 89-residue sequence from lacZ in the same reading frame from base 411 to 149 of pUC19.

pF3 was constructed as follows: a truncated cspA fragment (−280 to +243) was PCR-amplified from pJJG21 which was constructed from pJJG02 by creating an XbaI site at the SD sequence of cspA as follows: 5'-AATT<u>T</u>(A) <u>C</u>(T)TA<u>G</u>(A)AGGTAA-3' (the original nucleotides (SEQ ID NO: 9), in the parenthesis were substituted by the underlined nucleotides (SEQ ID NO: 10). The two primers for PCR were primer 3552 (5'-GACAGGATTAAAAATCGATG-3'). SEQ ID NO: 11 and 3551 (5' TTTAGAGCCATCGTCGTCAGGAG-3')SEQ ID NO:12. The fragment was cloned into the SmaI site of pUC19. As a result, the N-terminal 28-residue sequence of CspA was fused with a 54-residue sequence from lacZ which was resulted from +1 frame shift at base 414 of pUC19.

pF5 was constructed as a frameshift mutation by two-step PCR. In the first step, PCR was carried out with primer 3552 and primer 6879 [5'-ACGATACCAGTCGATTTTACCGGAC-3(SEQ ID NO: 13)]. In the second step, PCR was carried out using PCR1 product and 4860 [5'-CTGTCGACTTACTTACGGCGTTGC-3(SEQ ID NO: 14)] as primers. pJJG02 was used as the template for both PCR reactions. The resulting PCR product which has a C residue inserted at the second position of the fifth-codon of cspA, was then cloned into the SmaI site of pUC9. All the fusion constructs described above were confirmed by sequencing (Sanger et al., P.N.A.S., 74:5463–5467 (1977)).

pF2A was constructed as follows: a HindIII/SmaI fragment which contains the entire cspA gene was obtained from pJJG02 and cloned into pF2 digested with HindIii/HincII. Thus, the orientation of cspA is opposite to that of the fusion gene.

pF2B was constructed as follows: a 2.1 kb HindIII fragment which contains the entire B gene was obtained from pSJ7 (Lee et al., Mol. Microbiol., 11:833–839 (1994)) and cloned into pF2 digested with HindIII. The orientation of csvB is opposite to that of the fusion gene.

Figure 2:
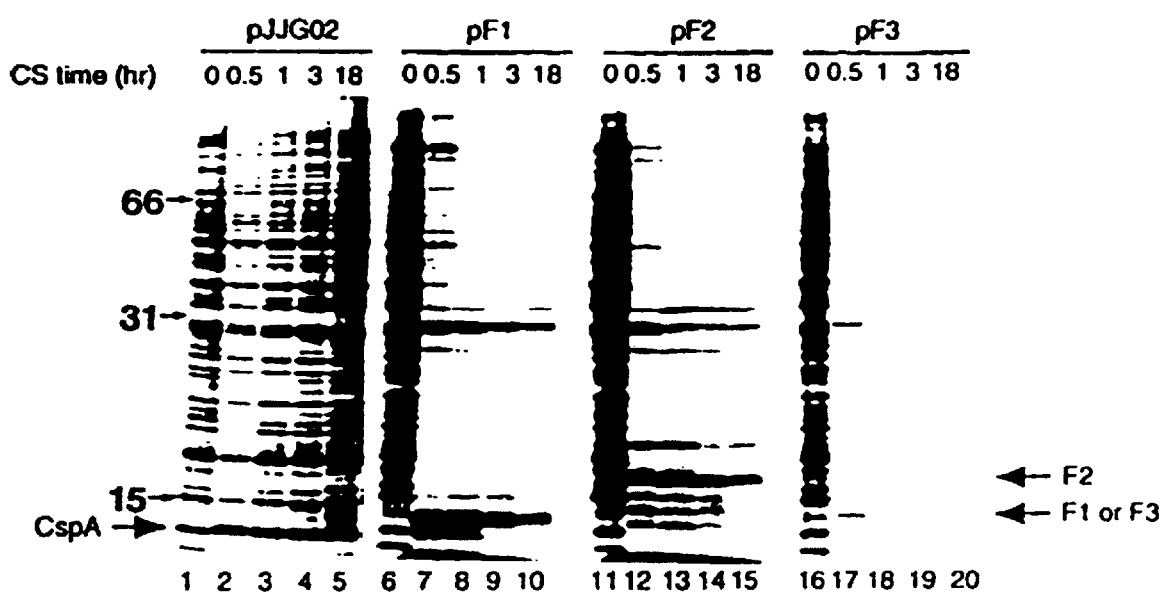
FIG. 2 shows inhibition of cellular protein synthesis by overexpression of the mRNA of the invention.

EXAMPLE 3
Inhibition of Cellular Protein Synthesis by Cold-Shock Induction of mRNA of the Invention E. coli cell CL83 transformed with different DNA constructs as described in Example 2 were pulse-labeled for 15 min with [$^{35}$S] methionine at 0, 0.5, 1, 3 and 18 hr after temperature downshift to 15° C. as described previously (Jiang et al. (1993)). The DNA constructs and the time points of labeling are indicated on the top of each lane. The protein synthesis pattern was analyzed by 17.5% SDS-PAGE, as shown in FIG. 2. The cell extract from a 0.25-ml cell culture was loaded. A: Lanes 1 to 5, cells with pJJG02; lanes 6 to 10, cells with pF1; lanes 11 to 15, cells with pF2; lanes 16 to 20, cells with pF3. The positions of CspA and the fusion proteins F1, F2, and F3 are indicated by the arrows. The positions of molecular weight markers (kDa) are shown at the right-hand side. B: Lanes 1 to 4, cells with pUC19; lanes 9 to 12, cells with pF5.

E. coli CL83 was transformed with the plasmids for the CspA fusion proteins and the production of cellular proteins was examined using [$^{35}$S] methionine after temperature downshift from 37 to 15° C. Total cellular proteins were then analyzed by SDS-PAGE as shown in FIG. 2. Cells carrying pJJG02 with the intact cspA gene produced little CspA if any at 37° C. (lane 1), while upon cold-shock CspA production was dramatically induced (lanes 2 and 3). It should be noticed that the production of total cellular proteins was significantly reduced at 30 min in contrast to a high level of cspA expression (lane 2). This is a typical cellular response during cold-shock adaptation. Cells recovered from growth inhibition after a few hours and cellular protein synthesis returned to full activity after 3 hr (lanes 4 and 5). Because pJJG02 is a multicopy plasmid carrying the intact cspA gene, CspA production was not reduced to a low basal level, even after 18 hr of cold shock, which usually occurs in normal cells.

For cells harboring three different CspA fusion constructs, the synthesis of cellular proteins at 37° C. was similar to that of pJJG02 (compare lanes 6, 11, and 16 with lane 1, FIG. 2). Upon temperature downshift, all three fusion proteins (F1, F2, and F3) were cold-induced as indicated by arrows. Surprisingly, the synthesis of almost all cellular proteins was severely inhibited throughout all time points examined at 15° C. (lanes 7 to 10, lanes 12 to 15, and lanes 17 to 20 for F1, F2, and F3, respectively), indicating that the cells were no longer capable of cold-shock adaptation. Besides the CspA fusion proteins, there is a major band in the middle of the gel, which was identified as β-lactamase, the product of the ampicillin-resistant gene (bla) in the plasmid used.

EXAMPLE 4
Inhibition of Cell Growth at Low Temperature

Figure 3:
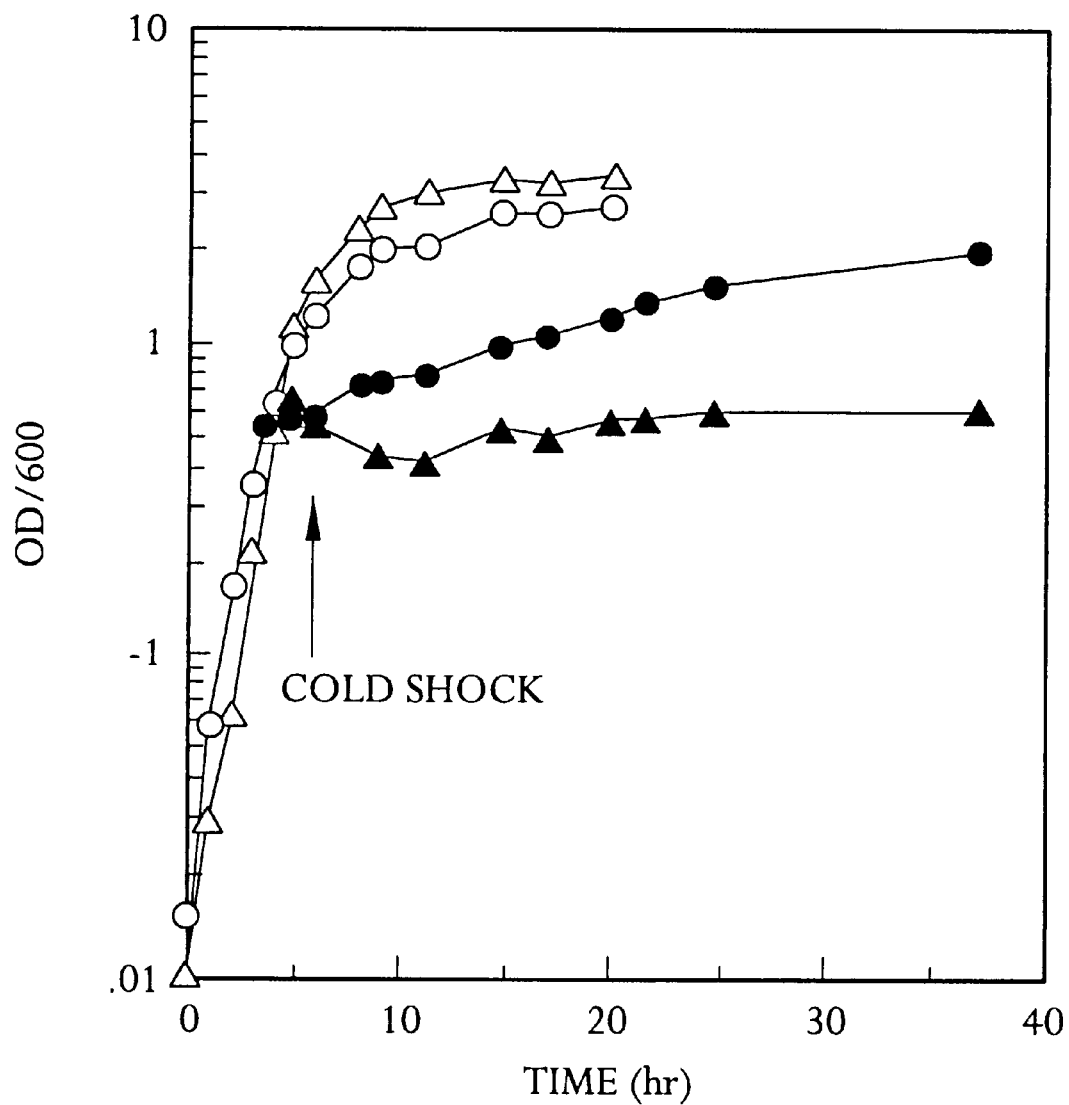
FIG. 3 shows inhibition of cell growth at low temperature due to cold-shock induced expression of the mRNA of the invention.

As shown in FIG. 3, CL83 cells transformed with pJJG02 or pF2 were grown at 37° C. in M9-Casamino acid medium. At mid-log phase ($OD_{600}$=0.6), the cell culture was divided into two. One was kept at 37° C., while the other was shifted to 15° C. Cell densities were measured at $OD_{600}$ by a Perkin-Elmer Spectrometer. pJJG02: °- - - - °, 37° C.; •- - - - •, 15°0 C. pF2: Δ- - - - Δ, 37°0 C.; ▲- - - - ▲, 15° C. Cells transformed with pF1 or pF3 behaved as did the cells transformed with pF2.

Figure 4:
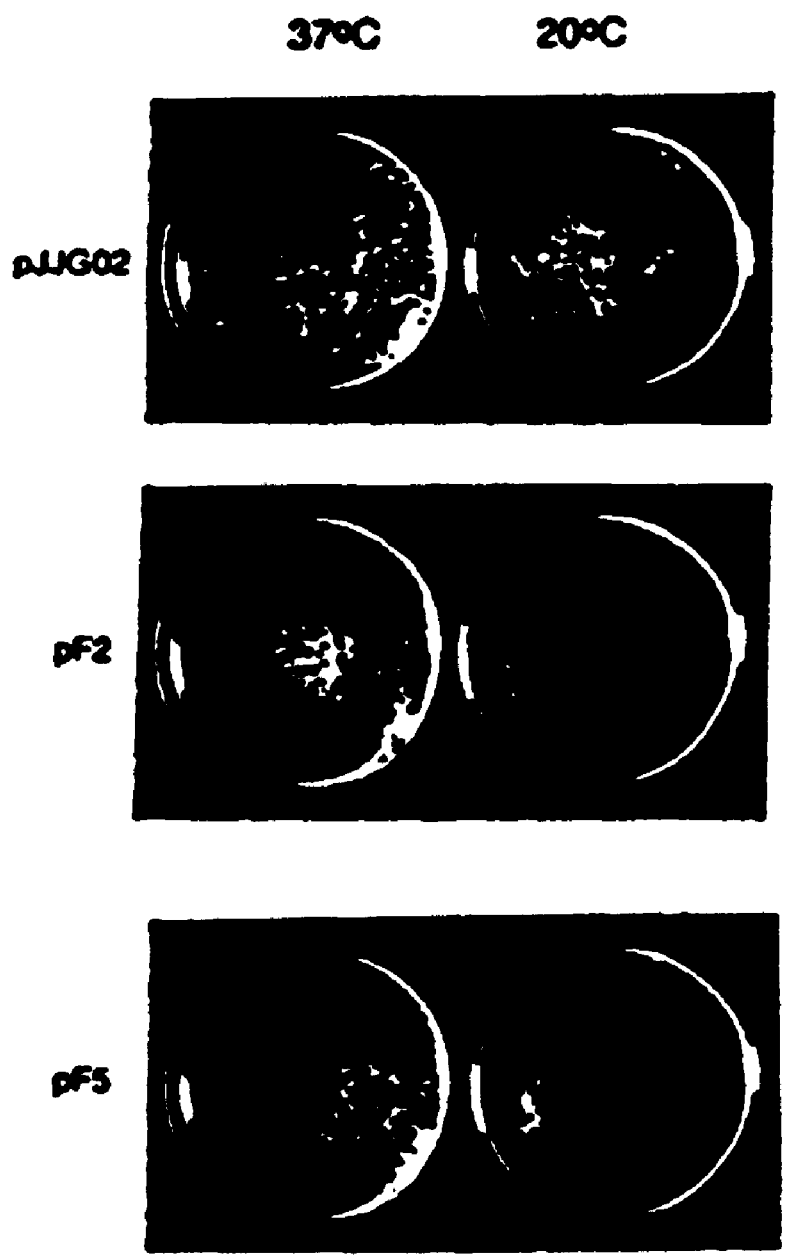
FIG. 4 shows the inhibitory effect of overexpression of the mRNA of the invention on bacterial colony formation.

EXAMPLE 5
Effect of Overexpression of the mRNA of the Invention on Bacterial Colony Formation CL83 cells harboring the different plasmids were grown in L-broth medium supplemented with ampicillin (50 μg/ml) at 37° C. At mid-log phase, cells were plated on two L-broth agar plates with ampicillin (50 μg/ml). One plate was incubated at 37° C. for 12 hr and the other at 20° C. for 36 hr. FIG. 4 shows inhibition at cold-shock temperature of colony growth of bacteria harboring plasmids pF2 or pF5. Growth of bacteria harboring plasmids pF1 or pF3 was likewise inhibited.

Figures 5A, 5B:
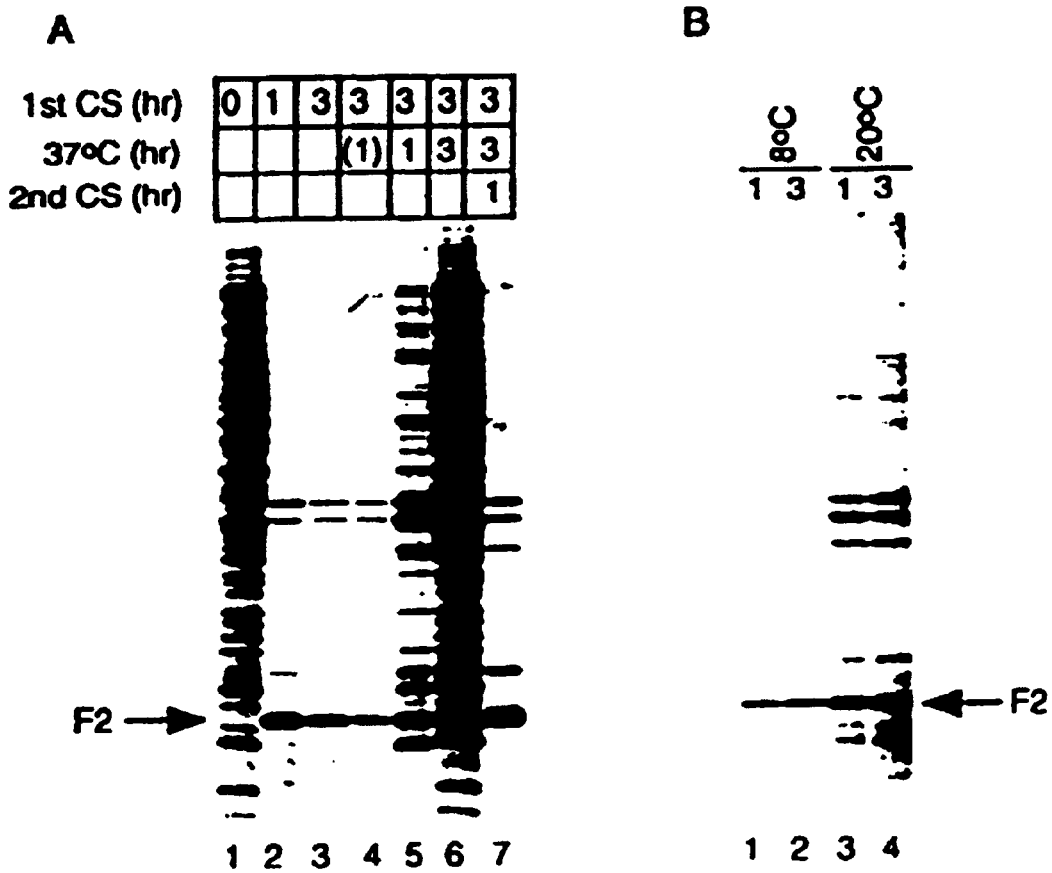
FIGS. 5A and B shows the suppression of bacterial proteins after down-shift of temperature from 37° C. to 15° C., and the effects of other temperature changes.

EXAMPLE 6
Low Temperature Expression of the mRNA of the Invention Suppresses Bacterial Protein Production When CL83 cells harboring pF2 were shifted from 37 to 15° C., F2 production was dramatically induced and cellular protein synthesis was almost completely blocked (FIG. 5A; lanes 2 and 3). When cells were first labeled at 3 hr at 15° C. followed by chasing the labeled production for another 1 hr at 37° C., the F2 band can still be detected (lane 4), indicating that F2 is quite stable at 37° C. In another experiment, after the cells were first cold-shock (CS) treated for 3 hr at 15° C., the culture was shifted back to 37° C., and after 1 hr incubation at 37° C., cells were pulse-labeled. As shown in lane 5, the synthesis of cellular proteins was mostly recovered and F2 was still produced at a relatively high level. This result demonstrates that the expression at 37° C. of a DNA encoding the mRNA of the invention, at which temperature the mRNA is unstable, had no inhibitory effects on cellular protein synthesis. If pulse-labeled at 3 hr after shifting back to 37° C., no more F2 was synthesized and cellular protein synthesis was completely restored (lane 6). In order to confirm the cells still harbored the pF2 plasmid, the cells were shifted back to 15° C. for the second time, again F2 production was induced and the cellular protein synthesis was blocked (lane 7). These results demonstrate that the inhibitory effects by the expression of the DNA encoding the mRNA are exerted only at low temperatures, under the conditions used.

Figure 6:
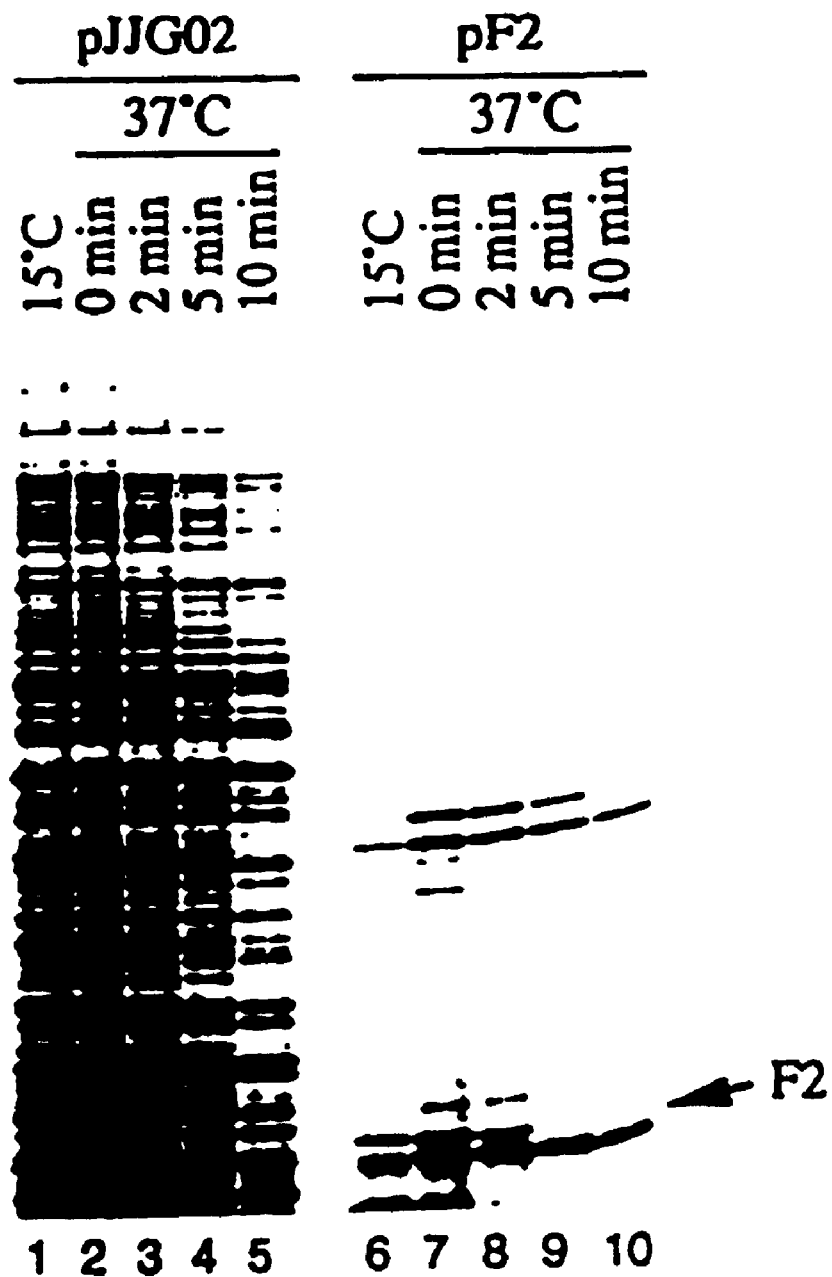
FIG. 6 shows the translation of endogenous mRNAs from cells overexpressing the exogenous mRNA of the invention.

EXAMPLE 7
Translation of Endogenous mRNAs From Cells Overexpressing the mRNA of the Invention Cells carrying pF2 were first cold-shock treated for 3 hr at 15° C. Rifampicin (200 μg/ml) was then added to the culture, and after 10 min incubation the culture was shifted back to 37° C. The cells were then pulse-labeled with [$^{35}$S] methionine for 5 min at 0 (lane 7, FIG. 6), 2 (lane 8), 5 (lane 9) and 10 min (lane 10) after the temperature shift. A similar labeling experiment was carried out as a control with the cells harboring pJJG02 (lanes 1 to 5, FIG. 7). As shown in lane 1, the control cells were well adapted to 15° C. after 3 hr incubation producing all cellular proteins, while cells with pF2 were strongly inhibited from producing bacterial proteins, producing mainly the F2 fusion protein and β-lactamase (lane 6). After the addition of rifampicin, very similar patterns of protein synthesis to that at 15° C. (compare lanes 2 to 5 with lane 1) were obtained for the cells with pJJG02, indicating that the same mRNAs were used before and after the addition of rifampicin. In the case of cells with pF2, major proteins produced at 37° C. after the addition of rifampicin (lanes 7–10) were identical to those produced by the translation inhibited cells (lane 6), indicating that except the mRNAs used for translation in the translation inhibited cells, no other cellular mRNAs existed in the cells. These results indicate that almost all polysomes in the cells in which translation of bacterial mRNAs was inhibited by the method of the invention were occupied with the mRNA of the invention.

All references referred to herein are incorporated by reference.

As will be apparent to those skilled in the art, in light of the foregoing description, many modifications, alterations, and substitutions are possible in the practice of the invention without departing from the spirit or scope thereof. It is intended that such modifications, alterations, and substitutions be included in the scope of the claims.

What is claimed is:

1. A method for inhibiting protein translation in a bacterium comprising over expressing in the bacterium an mRNA which comprises a translational initiation codon and a downstream box (DSB) nucleotide sequence from a cold shock inducible gene, which DSB is complementary to the anti-DSB of the 16S rRNA of the bacterium, and allowing the mRNA to anneal to the anti-DSB, thereby occupying all the ribosome of said bacterium and inhibiting translation of other bacterial mRNAs by exposing the bacterium to cold shock by reducing the temperature from the physiological growth temperature to below physiological growth temperature of the bacterium.

2. The method of claim 1 wherein the overexpressing is by transforming the bacterium with a cloning vector containing a DNA sequence which transcribes the mRNA.

3. The method of claim 2 wherein the DNA contains a promoter sequence 5' to the mRNA transcribing sequence.

4. The method of claim 1 wherein the initiation codon is selected from the group consisting of AUG, GUG, and UUG.

5. The method of claim 1 wherein the downstream box sequence overlaps the initiation codon.

6. The method of claim 1 wherein the downstream box is positioned 3' to the initiation codon at a distance between 0 and 30 nucleotides from the 3' end of the initiation codon.

7. The method of claim 6 wherein the distance is between 9 and 15 nucleotides.

8. The method of claim 1 wherein the downstream box is between 6 and 20 nucleotides in length.

9. The method of claim 8 wherein the downstream box is between 8 and 14 nucleotides in length.

10. The method of claim 1 wherein the bacterium is E. coli.

11. The method of claim 1 wherein the mRNA comprises an untranslated region 5' to the initiation codon.

12. The method of claim 11 wherein the untranslated region comprises a Shine-Dalgarno region.

13. The method of claim 1 wherein the mRNA comprises, 3' to the downstream box, a sequence which encodes a polypeptide.

14. The method of claim 1 which comprises exposing the bacterium to cold shock by reducing the temperature from the physiological growth temperature to below 20° C.

15. The method of claim 14 wherein the temperature reduction is to below 15° C.

16. An RNA construct comprising a translational, initiation codon and a downstream box (DSB) nucleatide sequence of a cold shock inducible bacterial gene 3' to the initiation codon, which DSB is complementary to the anti-DSB of the 16S rRNA of the bacterium, which construct has the sequence 5'-AUGX$_{(n)}$AUGACUGGUAUCGU-3' wherein "n" is a whole number from 0 to 30, and X is G, C, U or A, wherein X is the same or different from any other occurrence of X, wherein the sequence is identified by SEQ ID NO. 7, wherein the RNA is an isolated RNA construct or is transcribed from an isolated DNA construct, which RNA inhibits protein translation in a bacterium under condition of cold shock at a temperature below the physiological growth temperature of the bacterium and is stable at that temperature.

17. The RNA construct of claim 16 wherein the initiation codon is selected from the group consisting of AUG, GUG, and UUG.

18. The RNA construct of claim 16 wherein the downstream box sequence overlaps the initiation codon.

19. The RNA construct of claim 16 wherein the downstream box is positioned 3' to the initiation codon at a distance between 0 and 30 nucleotides from the 3' end of the initiation codon.

20. The RNA construct of claim 19 wherein the distance is between 9 and 15 nucleotides.

21. The RNA construct of claim 20 wherein the distance is 12 nucleotides.

22. The RNA construct of claim 16 wherein the downstream box is between 6 and 20 nucleotides in length.

23. The RNA construct of claim 16 wherein the downstream box is selected from the group consisting of AUGACUCGUAUCGU (SEQ ID NO:15), AUGACUG-GUUUCGU (SEQ ID NO:3), AUGACUGGUUUAGU (SEQ ID NO:4), AUGAGUUAUGUAGA (SEQ ID NO:5), and AUGGCGAAAAGAAU (SEQ ID NO:6).

24. The isolated RNA construct of claim 16 wherein the anti-downstream box has the sequence UACUUAGUGU-UUCA (SEQ ID NO:16).

25. The RNA construct of claim 16 selected from the group consisting of AUGACUGGUAUCGU, AUGACUGGUUUCGU, AUGACUGGUUUAGU, AUGAGUUAUGUAGA, and AUGGCGAAAAGAAU, which sequences are identified by SEQ ID NO. 2, SEQ ID NO. 3, SEQ ID NO. 4, SEQ ID NO. 5, and SEQ ID NO. 6, respectively.

26. An isolated DNA construct comprising a translational initiation codon and a downstream (DSB) box nucleotide sequence 3' to the initiation codon of a cold shock inducible bacterial gene, which DSB, is complementary to the anti-DSB of the 16S rRNA of the bacterium, which construct has the sequence 5'-ATGY$_{(n)}$ATGACTTGGTATCGT-3', wherein "n" is a whole number from 0 to 30, Y is G, C, T, or A, and wherein Y is the same or different from any other occurrence of Y, wherein the sequence is identified by SEQ ID NO. 8, which construct produces an RNA transcript which is unstable at physiological growth temperature of the bacterium, which inhibits protein translation in the bacterium at temperatures below the physiological growth temperature of the bacterium, and is stable at that temperature.

27. The isolated DNA construct of claim 26 which further comprises a promoter element 5' to the initiation codon.

28. The isolated DNA construct of claim 26 wherein the initiation codon is selected from the group consisting of AUG, GUG, and UUG.

29. The isolated DNA construct of claim 26 wherein the downstream box sequence overlaps the initiation codon.

30. The isolated DNA construct of claim 26 wherein the downstream box is positioned 3' to the initiation codon at a distance between 0 and 30 nucleotides from the 3' end of the initiation codon.

31. The isolated DNA construct of claim 30 wherein the distance is between 9 and 15 nucleotides.

32. The isolated DNA construct of claim 31 wherein the distance is 12 nucleotides.

33. The isolated DNA construct of claim 26 wherein the downstream box is between 6 and 20 nucleotides in length.

34. The isolated DNA construct of claim 26 which contains a Shine-Dalgarno region 5' to the initiation codon.

35. The DNA construct of claim 26 wherein the DNA sequence coding for the downstream box is selected from the group consisting of ATGACTGGTATCGT, ATGACTGGTTTCGT, ATGACTGGTTTAGT, ATGAGTTATGTAGA, and ATGGCGAAAAGAAT, wherein the sequences are identified by SEQ ID NO 17, SEQ ID NO 18, SEQ ID NO 19, SEQ ID NO 20 and SEQ ID NO 21.

36. A cloning vehicle which comprises a DNA promoter sequence operably linked to a DNA sequence, a downstream box (DSB) of a cold shock inducible bacterial gene which DSB is complementary to the anti-DSB of the 16S rRNA of the bacterium, which DNA sequence 5'-ATGY$_{(n)}$ATGACTTGGTATCGT-3', wherein "n" is a whole number from 0 to 30, Y is G, C, T, or A, and wherein Y is the same or different from any other occurrence of Y, wherein the sequence is identified by SEQ ID NO. 8 and a translational initiation codon upstream from the DSB, which replication vehicle produces an RNA transcript which is unstable at physiologcal growth temperature of the bacterium, which inhibits protein translation in a bacterium at a temperature below the physiological growth temperature of the bacterium, and is stable at that temperature.

37. A bacterium which has been transformed with the cloning vector of claim 36.

38. An RNA construct comprising an initiation codon and a downstream box nucleotide sequence 3' to the initiation codon which sequence is complementary to the anti-downstream box of the 16 S RNA of a bacterium, wherein the RNA is an isolated RNA construct or is transcribed from an isolated DNA construct, wherein the sequence of the downstream box is selected from the following group of sequences consisting of 5'-AUGACUGGUAUCGU, AUGACUGGUUUCGU, 5'-AUGACUGGUUUAGU-3', 5'AUGAGUUAUGUAGA-3'; and 5'-AUGGCGAAAAGAAU-3', which sequences are identified by SEQ ID NO. 2, SEQ ID NO. 3, SEQ ID NO. 4, SEQ ID NO. 5, and SEQ ID NO. 6, respectively.

39. An isolated RNA construct which is complementary to the sequence of the bacterial cold shock inducible gene, said RNA comprising in the following order, a 5'-untranslated RNA sequence which is susceptible to dearation at physiolocalcal growth temperature, a translational initiation codon, and a downstream box (DSB) which either overlaps with, or resides downstream from the initiation codon, which DSB is complementary to the anti-DSB of the 16S rRNA of the bacterium, is unstable at physiological growth temperature and stable at that temperature, which RNA inhibits translation of the proteins in the bacterium under conditions which induce the cold shock inducible genes of the bacterium.

40. An isolated DNAconstruct comprising a portion of a bacterial cold shock inducible gene, which DNA codes for and comprises in the following order, a 5'-untranslated sequence which is susceptible to degration at physioloaical growth temperature, a translational initiation codon downstream from said untranslated sequence and a downstream box (DSB) which either overlaps with, or resides downstream from the initiation codon, which DSB is complementary to the anti-DSB of the 16S rRNA of the bacterium, which construct is competent to produce an RNA transcript which is unstable at physiological growth temperatures and stable at that temperature which RNA inhibits translation of the proteins in the bacterium under conditions which induce the cold shock inducible genes of the bacterium.

41. A cloning vehicle comprising a DNA promoter operably linked to the DNA construct of claim 40, which when transformed into a competent host bacterium, expresses the RNA transcript which inhibits the translational proteins in the bacterium under temperature conditions which induce the cold shock inducible genes of the bacterium.

* * * * *